(12) United States Patent
Takahashi et al.

(10) Patent No.: US 6,297,045 B1
(45) Date of Patent: Oct. 2, 2001

(54) MASTITIS DIAGNOSING APPARATUS

(75) Inventors: Hideyuki Takahashi, Ibaraki; Takahisa Matue, Chiba; Masakatu Shimizu, Tokyo, all of (JP)

(73) Assignees: Japan as represented by National Institute of Animal Health, Ministry of Agriculture, Forestry and Fishers, Director General, Tukuba; Hideyuki Takahashi, Tuchiura; Tokken, Inc., Yachiyo, all of (JP)

( * ) Notice: Subject to any disclaimer, the term of this patent is extended or adjusted under 35 U.S.C. 154(b) by 0 days.

(21) Appl. No.: 09/368,451

(22) Filed: Aug. 4, 1999

(30) Foreign Application Priority Data

Aug. 4, 1998 (JP) .................................. 10-219508

(51) Int. Cl.$^7$ ..................................................... C12M 1/34
(52) U.S. Cl. .................................. 435/288.7; 435/287.3; 435/303.3
(58) Field of Search .................... 435/8, 287.3, 288.1, 435/288.7, 808, 303.3

(56) References Cited

U.S. PATENT DOCUMENTS

| | | | |
|---|---|---|---|
| 4,349,510 | * | 9/1982 | Kolehmainen et al. . |
| 4,390,274 | * | 6/1983 | Berthold et al. . |
| 5,234,684 | * | 8/1993 | Sordillo et al. . |
| 6,031,367 | * | 2/2000 | Mangan . |

FOREIGN PATENT DOCUMENTS

| | | | |
|---|---|---|---|
| 2 001 434 | * | 1/1979 | (GB) . |
| 5-184350 | | 7/1993 | (JP) . |
| 6-181743 | | 7/1994 | (JP) . |

OTHER PUBLICATIONS

E–M. Lilius, et al., "Use of Inflammatory Cell Activities in Bovine Milk to Diagnose Mastitis", Am. J. Vet. Res., vol. 51, No. 10, Oct. 1990, pp. 1527–1533.

Takahashi et al., "Manual for High–Quality Milk Production by Environmental Stress Reduction", Mar. 1997, pp. 33–42.

Japanese Argument Against the Notification of Reason for Refusal and its English translation. (Two Japanese Pat. Applns. noted therein are cited above and enclosed.) No Date Provided.

* cited by examiner

Primary Examiner—William H. Beisner (57) ABSTRACT

In a mastitis progression data memory 80 there is previously recorded data on the corresponding relationship between the state of progression of mastitis caused by bacteria and the trace light intensity chemically emitted by phagocytic leukocytes in milk when they phagocytose the bacteria, the trace light intensity chemically emitted by the phagocytic leukocytes in the milk is detected by a photodetector 41a, the state of progression of mastitis corresponding to the light intensity is diagnosed by an extractor/converter 13 with reference to the mastitis progression data memory 80 based on the detected trace light intensity, and the diagnosed state of progression of mastitis is outputted by output means 30. It is possible to conveniently and reliably diagnose the state of progression of mastitis from invasion of bacteria up to severe mastitis.

9 Claims, 9 Drawing Sheets

MASTITIS DIAGNOSING APPARATUS

FIELD OF THE INVENTION AND RELATED ART STATEMENT

The present invention relates to a mastitis diagnosing apparatus, and particularly it relates to a mastitis diagnosing apparatus that is capable of easily measuring the state of progression of mastitis based on a chemiluminescence method (CL activity measurement).

The incidence of mastitis among dairy cows in Japan hovers between 20–25% of all dairy cow diseases, and it has the highest mortality rate. Mastitis is the disease to which dairy cows are most susceptible, and it is also a very difficult disease to cure. Appropriate methods are being sought for dealing with mastitis, through early discovery of the diseased condition and optimum treatment based on the course (state of progression) of the mastitis.

Various conventional methods are known for diagnosis of mastitis.

Figure 9:
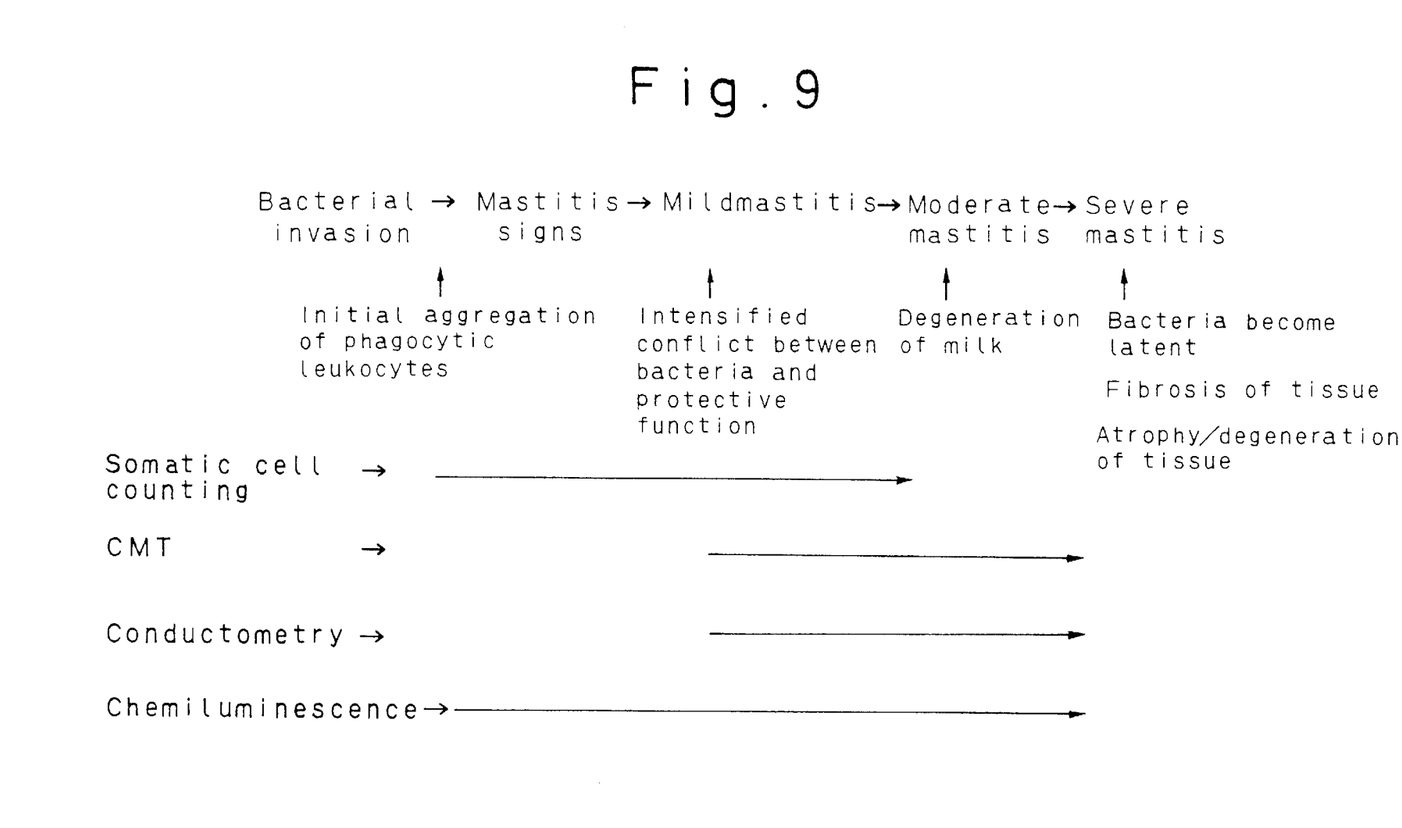
FIG. 9 is an illustrative representation of the range of effectiveness of the major conventional diagnostic methods for the state of progression of mastitis.

FIG. 9 is a diagram showing the relationship between progression of mastitis and effectiveness of the major diagnostic methods. As shown in FIG. 9, mastitis usually takes a course from bacterial invasion→mastitis signs→mild mastitis→moderate mastitis→severe mastitis. Common diagnostic methods for mastitis include somatic cell counting, CMT (California Mastitis Test), conductometry, etc., among which somatic cell counting is effective for diagnosis from bacterial invasion up to moderate mastitis, and CMT and conductometry are effective for diagnosis from mild mastitis up to severe mastitis.

Somatic cell counting involves measurement of the number of cells in milk, including lactic gland epithelial cells, neutrophils, acidophils and other phagocytes, and lymphocytes, monocytes, plasma cells and the like, and it can successfully detect during the period from initial infection up to moderate mastitis.

CMT is a method of estimating the number of somatic cells by utilizing the difference in the extent of aggregation reaction depending on the number of somatic cells, when a surfactant is added to the milk. Since a BTB reagent is also included for pH measurement, it is used as an evaluation index for mastitis by utilizing the fact that increased vascular permeability and accelerated conflict between leukocytes and bacteria during mastitis results in increased salts such as sodium chloride and potassium chloride in the milk, creating a higher alkalinity, and causing a color change from yellow→green→blue. The advantages of this measurement are that it can be easily performed by anyone, it can generally distinguish between the presence or absence of mastitis, and it is an extremely low-cost method.

Conductometry takes advantage of the fact that mastitic milk has greater vascular permeability and contains more electrolyte components such as sodium, chlorine and other plasma components due to inflammation reaction in the mammary tissue, thus allowing electricity to flow more readily than with normal milk, and its advantage is that an objective value can be obtained by quantifying the conductivity.

Milk cell counters exist for somatic cell counting, but their problems are high cost and the excessive labor required for smear measurement using optical microscopes. For the colostrum in particular, it has been difficult to the smear and fix the milk. Another problem is that as mastitis progresses, numerous leukocytes adhere to the bacteria producing bulb-like forms which make measurement impossible.

The drawbacks of CMT are that diagnosis is difficult until the reaction has occurred, involving the conflict between leukocytes and the bacteria, or after promotion of vascular permeability, and that diagnosis depends on subjective human judgment, so that this method can only serve as an approximate diagnosis method. Diagnosis has been particularly rough in cases where the milk somatic cell count is 300,000/ml or less.

Conductometry has had disadvantages in that it depends on changes occurring by inflammation reaction after the bacteria invade and conflict with the leukocytes, and therefore it is unsuitable for diagnosis in the initial stages of mastitis, while it has poor reproducibility due to substantial differences in electrolyte components and concentrations in different teats or different cows even with normal milk, such that diagnosis is risky by this diagnostic method alone.

Thus, one of the present inventors, Hideyuki Takahashi, focusing on the fact that phagocytic leukocytes such as neutrophils which constitute the larger part of somatic cells in milk mount an excellent initial reaction (mobilization) during infection, has already proposed a method for diagnosis of mastitis (chemiluminescence method) by measurement of phagocytic leukocyte function in milk in terms of CL activity (Takahashi, Hideyuki, "Manual for High-Quality Milk Production by Environmental Stress Reduction", ed. Hokkaido National Agricultural Experimental Station, March, 1997).

This chemiluminescence method (CL activity measurement) will now be explained. Milk contains somatic cells such as lactic gland epithelial cells, neutrophils, acidophils, lymphocytes, monocytes, plasma cells, etc. These cells are virtually absent in milk during times of health, but once the mamma suffers invasion of bacteria, leukocytes with phagocytic bactericidal activity (phagocytic leukocytes=neutrophils, acidophils, etc.) accumulate in the milk in an attempt to halt bacterial proliferation. Among these, it is the neutrophils that mobilize to the greatest extent after bacterial invasion, working to halt proliferation of the bacteria by overwhelming superiority of numbers. The neutrophils kill bacteria mainly with active oxygen, and also emit a trace intensity of light (photons) in proportion to the amount of active oxygen released.

Chemiluminescence is a method whereby that light (of photons) is detected, amplified and quantified, and it is characterized in that the phagocytic leukocytes with bactericidal activity that accumulate in response to bacterial invasion can be detected with high sensitivity during a long period from the initial bacterial invasion through to severe mastitis.

However, no apparatus (mastitis diagnosing apparatus) has yet been provided for convenient and reliable diagnosis of mastitis based on the aforementioned chemiluminescence method (CL activity measurement).

OBJECT AND SUMMARY OF THE INVENTION

It is an object of the present invention to provide a mastitis diagnosing apparatus capable of performing convenient and reliable diagnosis of the state of progression from invasion of bacteria into the mamma up to severe mastitis, based on chemiluminescence (CL activity measurement).

The mastitis diagnosing apparatus of the invention is characterized by comprising a memory for pre-storage of a corresponding relationship between the number of photons emitted when phagocytic leukocytes phagocytose bacteria in milk and the state of progression of mastitis due to the bacteria; photon counting means which counts within a prescribed period of time the number of photons emitted when phagocytic leukocytes in milk phagocytose bacteria, by addition of a culture solution, emission enhancer and phagocyte stimulator to the milk itself; diagnosing means which refers to the memory and, based on the number of photons counted by the photon counting means, diagnoses the state of progression of mastitis corresponding to the number of photons; and output means which allows output of the state of progression of mastitis diagnosed by the diagnosing means.

The mastitis diagnosing apparatus according to the invention is further characterized by comprising a memory for pre-storage of a corresponding relationship between the number of photons emitted when phagocytic leukocytes phagocytose bacteria in milk and the state of progression of mastitis due to the bacteria; reagent injection means which injects an emission enhancer and phagocyte stimulator into a set test tube in which the milk itself and a culture solution are mixed; stirring means which stirs with a prescribed period of stirring the test tube into which the emission enhancer and phagocyte stimulator have been injected from the reagent injecting means; incubation means which keeps the test tube stirred by the stirring means at a constant temperature; photon counting means which counts within a prescribed period of time the number of photons emitted when bacteria are phagocytosed by phagocytic leukocytes contained in the milk in the test tube incubated by the incubation means; diagnosing means which refers to the memory and, based on the number of photons counted by the photon counting means, diagnoses the state of progression of mastitis corresponding to the number of photons; and output means which allows output of the state of progression of mastitis diagnosed by the diagnosing means.

According to the present invention the design is such that there is pre-stored in the memory a corresponding relationship between the trace intensity of light chemically emitted when phagocytic leukocytes phagocytose bacteria in milk and the state of progression of mastitis due to the bacteria, a photodetector detects the trace intensity of light chemically emitted by the phagocytic leukocytes in the milk, the diagnosing means refers to the memory based on the detected trace intensity of light and diagnoses the state of progression of mastitis corresponding to the light intensity, and the output means outputs the diagnosed state of progression of mastitis; it therefore provides an effect that allows the state of progression from bacterial invasion of mastitis to severe mastitis to be conveniently and reliably diagnosed based on chemiluminescence (CL activity measurement).

According to the present invention the design is further such that there is pre-stored in the memory a corresponding relationship between the number of photons emitted when phagocytic leukocytes phagocytose bacteria in milk and the state of progression of mastitis due to the bacteria, the reagent injection means injects an emission enhancer and phagocyte stimulator into a set test tube in which the milk to be diagnosed and a culture solution are mixed, the stirring means stirs with a prescribed period of stirring the test tube into which the emission enhancer and phagocyte stimulator have been injected, the incubation means keeps the stirred test tube at a constant temperature, the photon counting means counts within a prescribed period of time the number of photons emitted when bacteria are phagocytosed by phagocytic leukocytes contained in the milk in the incubated test tube, the diagnosing means refers to the memory and, based on the counted photons, diagnoses the state of progression of mastitis corresponding to the number of photons, and the output means outputs the diagnosed state of progression of mastitis; it therefore provides an effect that allows the state of progression from bacterial invasion of mastitis to severe mastitis to be conveniently and reliably diagnosed based on chemiluminescence (CL activity measurement).

BRIEF DESCRIPTION OF THE DRAWINGS

FIGS. 4(A) and 4(B) are detailed structural diagrams of the stirrer of the mastitis diagnosing apparatus according to this embodiment, wherein 4(A) is a top view and 4(B) is a side view.

FIGS. 5(A) and 5(B) are detailed structural diagrams of the shutter of the mastitis diagnosing apparatus according to this embodiment, wherein 5(A) is a side view and 5(B) is a top view.

DETAILED DESCRIPTION OF THE PREFERRED EMBODIMENTS

Figure 1A:
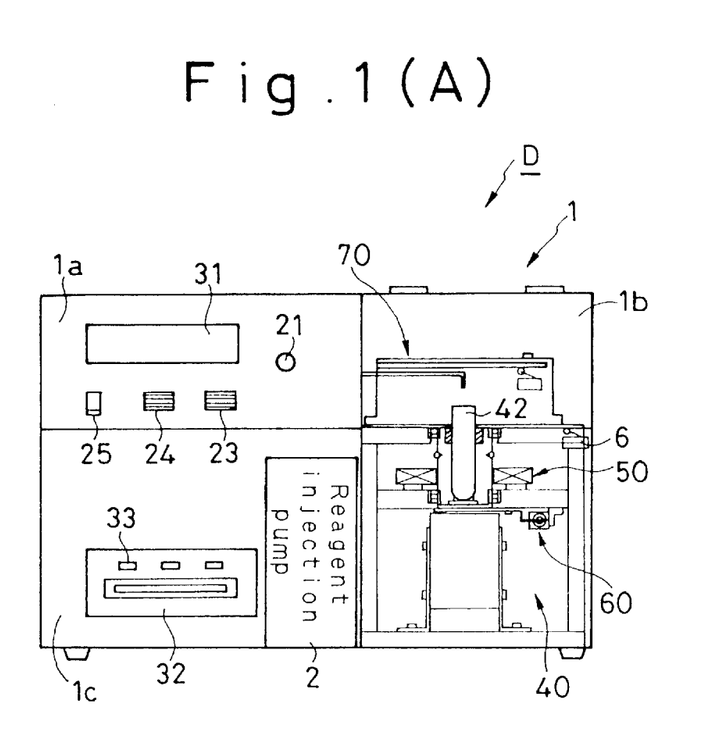
FIGS. 1(A) and 1(B) are full schematic diagrams of the mechanical system of a mastitis diagnosing apparatus according to an embodiment of the invention, wherein 1(A) is a see-through front view and 1(B) is a see-through side view.
Figure 1B:
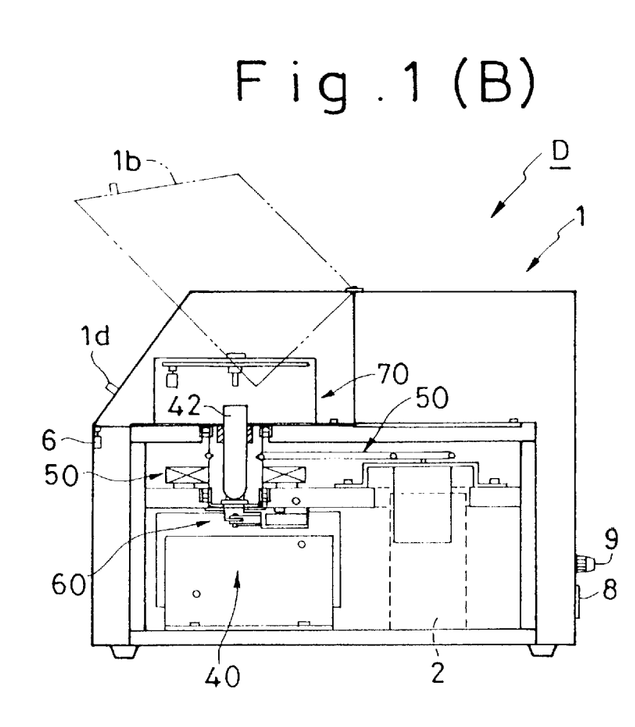
Figure 2A:
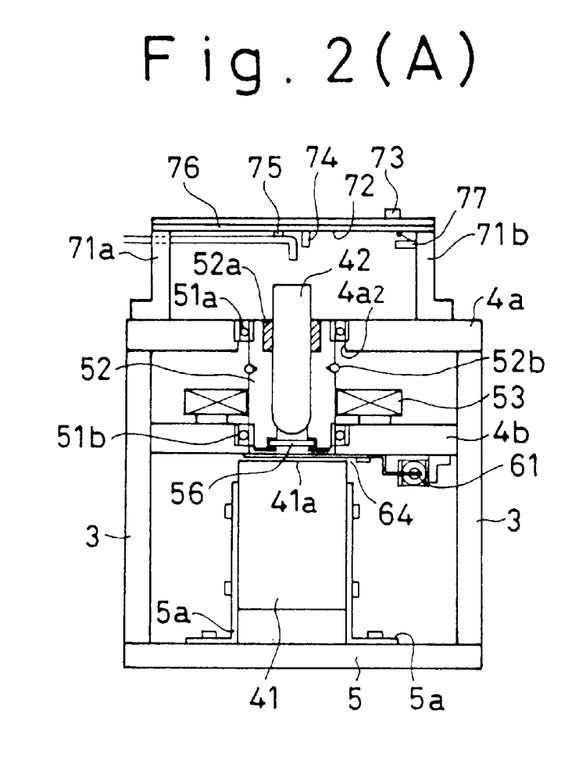
FIGS. 2(A) and 2(B) are enlarged diagrams of the mechanical system of the mastitis diagnosing apparatus according to this embodiment, wherein 2(A) is a cross-sectional front view and 2(B) is a cross-sectional side view.
Figure 2B:
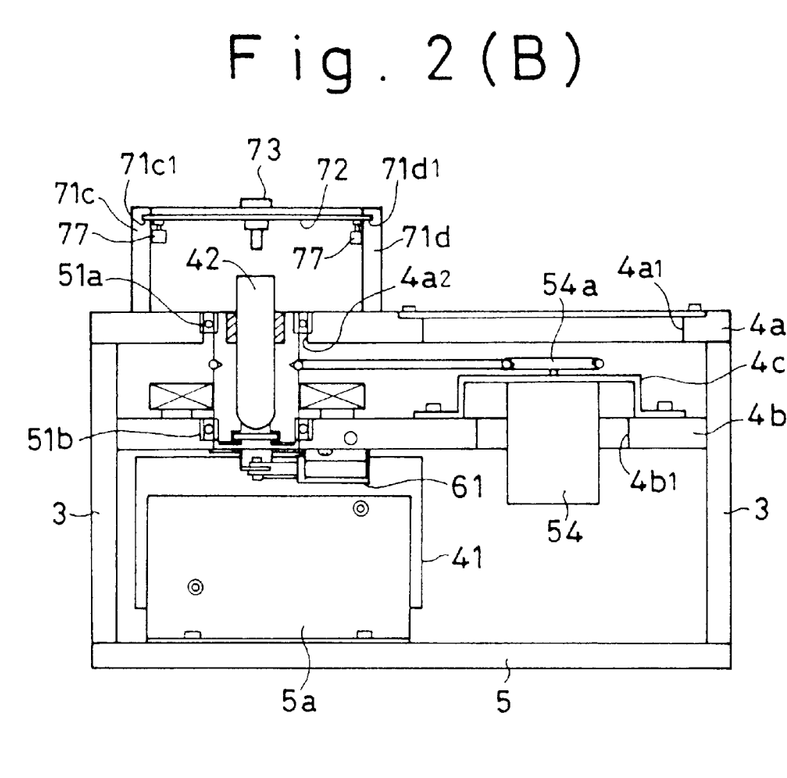
Figure 3:
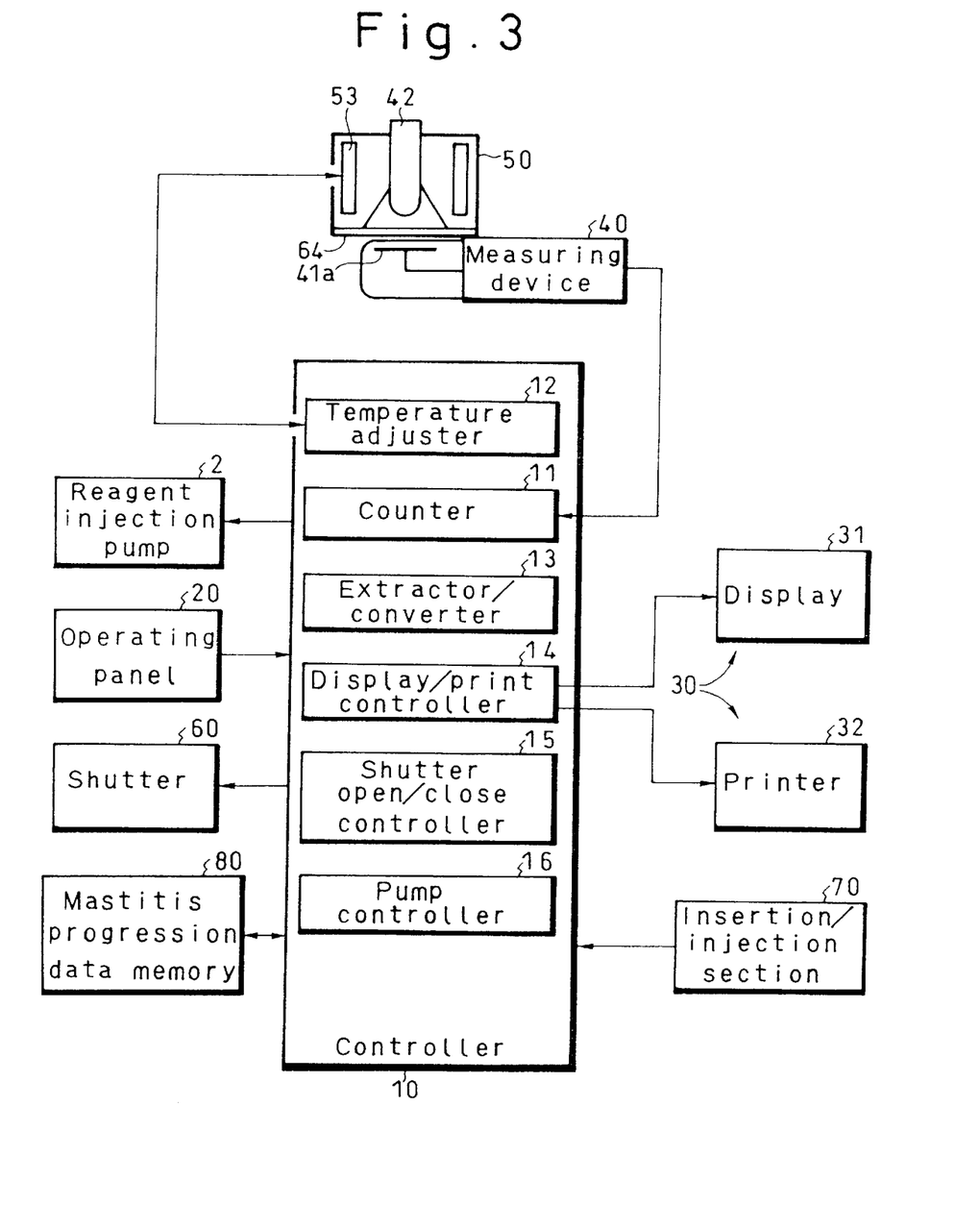
FIG. 3 is a block diagram of the control system of the mastitis diagnosing apparatus according to this embodiment.

FIG. 1 is a full schematic diagram of the mechanical system of a mastitis diagnosing apparatus D according to an embodiment of the invention, wherein (A) is a see-through front view and (B) is a see-through side view. FIG. 2 is an enlarged diagram of the mechanical system of the mastitis diagnosing apparatus D according to this embodiment, wherein (A) is a cross-sectional front view and (B) is a cross-sectional side view. FIG. 3 is a block diagram of the control system of the mastitis diagnosing apparatus D according to this embodiment.

As shown in FIGS. 1 to 3, the mastitis diagnosing apparatus D is provided with a start button 21, etc. in an operating panel 20 on the surface of a roughly rectangular frame 1, a display 31 for output of the measurement results and a printer 32 for printing out of the measurement results, and it internally houses the different members described below.

A slanted surface 1a is formed at the top front of the frame 1, and a cover 1b is supported at the right side of the slanted surface 1a with hinges in a rotatable manner. The cover 1b is made of a non-transparent synthetic resin material, which when opened allows observation of the interior. At the back of the frame 1 there are provided a connector 8 for connection of a cord to a commercial power source (100V AC) and a 100V AC fuse holder 9.

The structural parts of the operating panel 20 situated on the slanted surface 1a and the side 1c under it are a start button 21 to start measurement, a three-digit digital switch 23 for setting of the delay time after power-on, a three-digit digital switch 24 for setting of the stirring time, and a power on/off switch 25. The display 31 comprises a backlighted liquid crystal display device, and the printer 32 is provided with a print start button 33 which is pressed to select print output.

The frame 1 includes the following structural members. Specifically, they are a measuring device 40 which measures the photons emitted by milk in the test tube 42, a stirrer 50 which holds a test tube (sample cell) 42 containing milk and a reagent while stirring it by forward and reverse rotation, a shutter 60 between the bottom of the test tube 42 and the measuring unit 41 for open/close control of the passage of photons, an insertion/injection section 70 for insertion of the test tube 42 and injection of the reagent into the test tube 42, as well as additional parts. The additional parts are a reagent injection pump 2 used for injection of the reagent, a knob 1d used for opening and closing of the cover 1b, a microswitch 6 which detects whether the cover 1b is open or closed, and a support, cross board and base, which are explained below. The tank section of the reagent injection pump 2 separately includes luminol as the emission enhancer and zymosan as the phagocyte stimulator.

As shown in FIG. 3, the control system has a construction wherein the reagent injection pump 2, operating panel 20, output section 30, measuring device 40, stirrer 50, shutter 60, insertion/injection section 70 and mastitis progression data memory 80 are connected to a controller 10. The mastitis progression data memory 80 has previously recorded data on the corresponding relationship between the state of progression of mastitis and the number of photons emitted by phagocytic leukocytes, and determines the corresponding relationship using samples of states of progression of mastitis for reference.

The controller 10 comprises a CPU (Central Processing Unit), ROM (Read Only Memory), RAM (Random Access Memory), etc., and it is provided with a counter 11 which counts the number of photons emitted by phagocytic leukocytes such as neutrophils detected by a measuring unit 41 (FIG. 2(A)) equipped with a photodetector 41a consisting of a photoelectron multiplier tube for photon counting, a temperature adjuster 12 which maintains a temperature of 37±0.1° C. in the test tube 42 with a film heater 53, an extractor/converter 13 which extracts from the mastitis progression data memory 80 the state of progression of mastitis corresponding to the number of detected photons (trace light intensity) and converts the state of progression into a judgment value, a display/print controller 14 which controls output of the conversion result as a liquid crystal display or printed output, a shutter open/close controller 15 which controls opening and closing of the shutter 64, and a pump controller 16 which controls injection of the reagent from the reagent injecting pump 2.

Each of these structural members will now be explained in detail with reference to the drawings.

(1) Base, support, cross board, etc.

First, the base, support, cross board, etc. on which each of the members such as the measuring device 40 are mounted will be explained (FIGS. 2(A), (B)).

Supports 3 are mounted on each of the four corners of the rectangular base 5, and a top cross board 4a is fixed horizontally onto the supports 3 while a middle cross board 4b is fixed horizontally slightly above the middle. A rectangular window 4a1 is formed at the right of the top cross board 4a for adjustment of the belt of the stirrer 50 explained below, and a round hole 4a2 is formed toward the left for insertion of an upper bearing 51a for support of the rotating cylinder 52 of the stirrer 50.

Figure 4A:
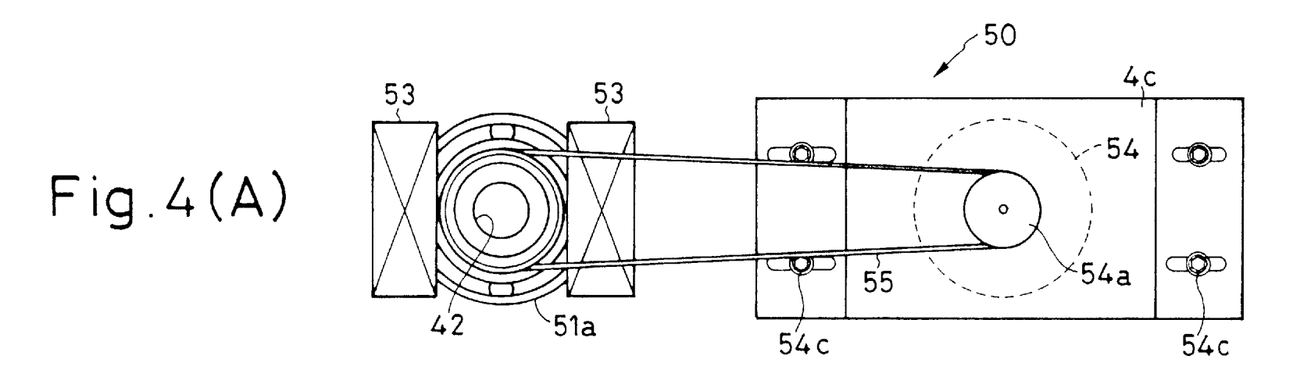
Figure 4B:
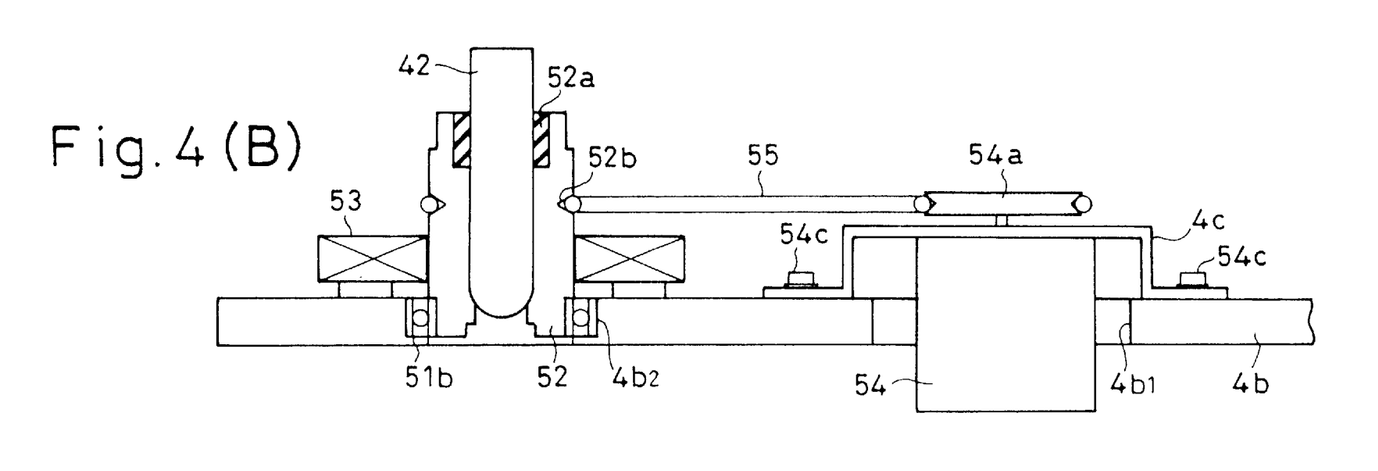

A circular escape hole 4b1 is formed at the right of the middle cross board 4b to allow passage of the motor 54 of the stirrer 50, and a hole 4b2 (see FIG. 4) is formed at the left for insertion of a lower bearing 51b for support of the rotating cylinder 52.

(2) Measuring device 40

As shown in FIG. 2, both sides of the measuring unit 41 of the measuring device 40 which has been rectangularly set on the base 5 are anchored with two L-shaped support plates 5a. On the top of the measuring device 40 there is placed the photodetector 41a which detects photons emitted from milk in the test tube 42.

(3) Stirrer 50

FIGS. 4(A) is a top view of the stirrer 50, and (B) is a side view thereof.

As shown in FIGS. 2 and 4, the outer ring of the upper bearing 51a and the outer ring of the lower bearing 51b are inserted in the hole 4a2 of the top cross board 4a and the hole 4b2 of the middle cross board, respectively. The cylindrical rotating cylinder 52 is inserted in the inner rings of the upper and lower bearings 51a, 51b. A ring-shaped anchoring rubber piece 52a which presses from above and adhesively anchors the test tube 42 is placed at the top of the rotating cylinder 52. The film heater 53 is situated in contact with the lower outer side of the rotating cylinder 52 to heat the milk in the test tube 42 through the rotating cylinder 52. The film heater 53 is equipped with a temperature detecting sensor (not shown), and it maintains a constant temperature (37±0.1° C.) through the temperature adjuster 12. The bottom of the test tube 42 is situated so as to be directly above the photodetector 41a of the measuring unit 41.

A reverse U-shaped brace 4c is anchored straddling the hole 4b1 of the middle cross board 4b, and a motor 54 consisting of a forward/reverse rotatable stepping motor or the like is anchored onto the brace 4c. A pulley 54a is anchored to the output shaft of the motor 54, and a belt 55 is looped between the pulley 54a and a V-groove 52b formed on the outer side of the rotating cylinder 52. The tension of the belt 55 is adjustable to the desired tension by loosening the screw 54c through the rectangular window 4a1 (FIG. 2(B)) and moving the brace 4c right and left. The test tube 42 in the rotating cylinder 52 is thus rotated in forward and reverse for stirring. The numeral 56 (FIG. 2(A)) is a protective glass which protects the photodetector 41a of the measuring unit 41.

(4) Shutter 60

Figure 5A:
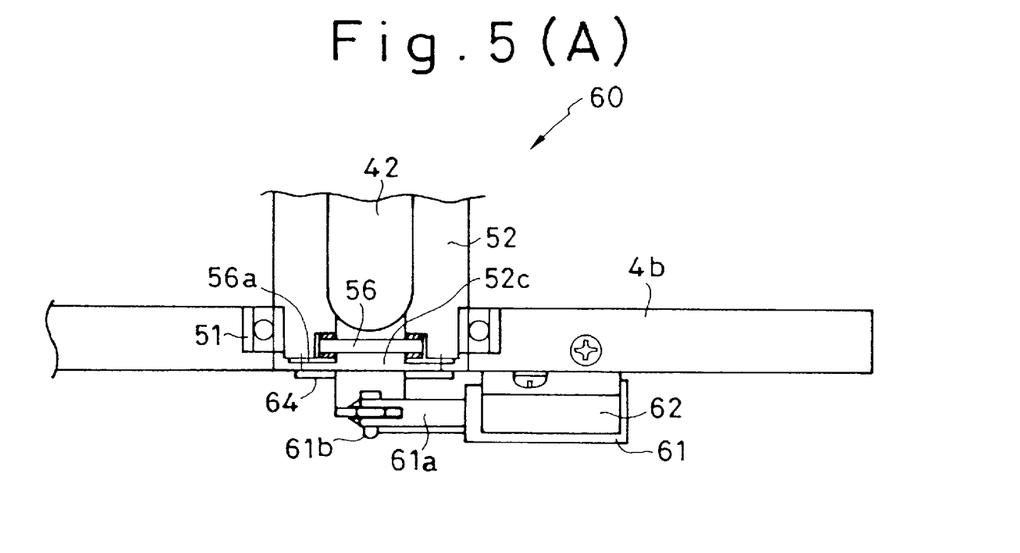
Figure 5B:
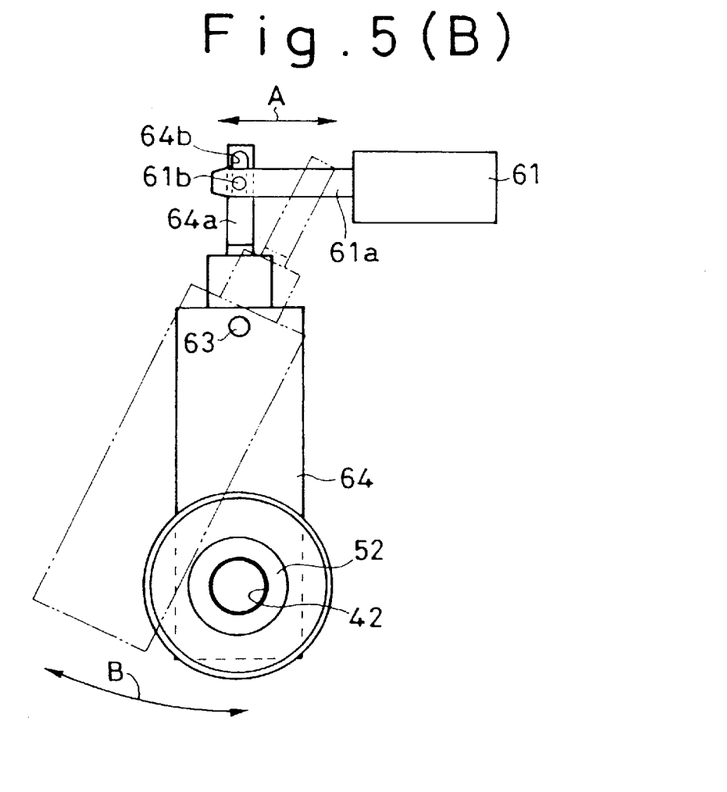

FIG. 5 is an enlarged view of the shutter 60, wherein (A) is a side view and (B) is a bottom view.

As shown in FIGS. 2 and 5, a solenoid 61 provided with an output shaft 61a that operates in the direction of arrow A is anchored to the bottom of the middle cross board 4b with an L-shaped mounting brace 62. On/off control of the solenoid 61 is accomplished by control of the shutter open/close controller 15 (FIG. 3). A pin 61b is fitted at the tip of the output shaft 61a, and the pin 61b is interlocked with a long hole 64b formed in an interlocking arm 64a of the shutter plate 64. The shutter plate 64 is rectangular, and is supported in a freely rotatable manner in the direction of arrow B by an axis pin 63 anchored to the middle cross board 4*b*. The shutter plate 64 has a width that totally covers and blocks light from the transmission window 52*c* formed at the bottom of the rotating cylinder 52 and the photodetector 41*a* of the measuring unit 41 (FIG. 2(A)). Operation of the output shaft 61*a* of the solenoid 61 in the direction of arrow A causes the shutter plate 64 to be manipulated in the direction of arrow B, and it is opened for only a prescribed time (for example, one minute) under the control of the shutter open/close controller 15, so that photons emitted from phagocytic leukocytes in milk can be detected by the photodetector 41*a* during that time only. Numeral 56*a* is a glass presser which presses against the above-mentioned protective glass 56.

(5) Test tube insertion/reagent injecting section (insertion/injection section) 70

FIG. 6 shows the insertion/injection section 70, and (A) is a top view with the sliding lid open, (B, E) are side views, (C) is a bottom view with the sliding lid shut and (D) is a bottom view with the sliding lid open.

As shown in FIGS. 2 and 6, the rotating cylinder 52 is set so as to be covered with the box-shaped insertion/injection section 70. That is, four side walls 71*a*–71*d* are anchored in rectangular arrangement around the hole 4*a*2 formed in the top cross board 4*a*, and slide grooves are formed in the tops of the side walls 71*c*, 71*d*. A rectangular sliding lid 72 is inserted in a freely slidable manner in this slide groove. A knob 73 is provided at the top right end of the lid 72, to allow right/left opening and closing of the lid 72 (FIG. 2(A), FIG. 6).

Two pipes 76*a*, 76*b* arranged in parallel and connected to the reagent injection pump 2 (FIG. 1) in the insertion/injection section 70 are drawn along the ceiling, the ends of the pipes 76*a*, 76*b* being bent in an L-shaped manner, and their tips are placed so as to be directly above the test tube 42. The end sections of the pipes 76*a*, 76*b* are made of a restorable elastic material such as vinyl chloride.

Figure 6A:
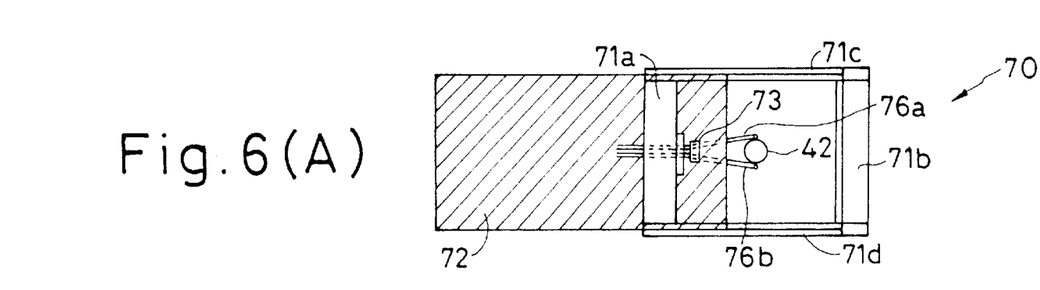
FIGS. 6(A)–6(E) are illustrations of the detailed structure and operation of the test tube insertion/reagent injection section of the mastitis diagnosing apparatus according to this embodiment, wherein 6(A) is a top view with the lid open, 6(B, E) are side views with the lid shut, 6(C) is a bottom view with the lid shut and 6(D) is a bottom view with the lid open.
Figure 6B:
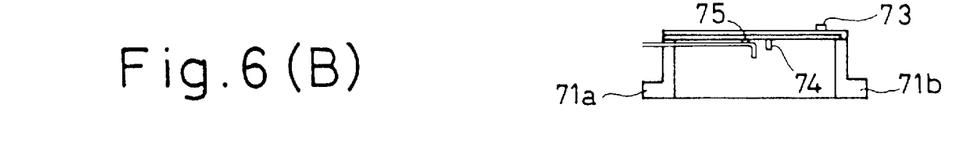
Figure 6C:
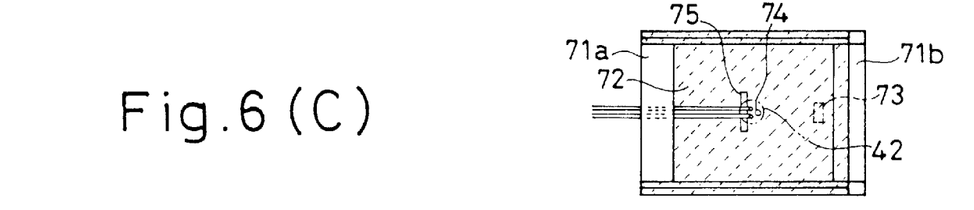
Figure 6D:
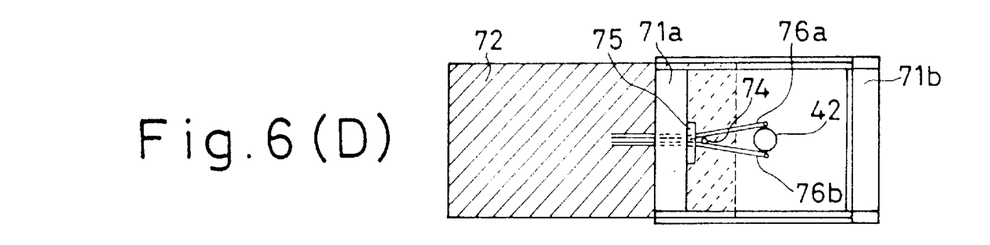
Figure 6E:
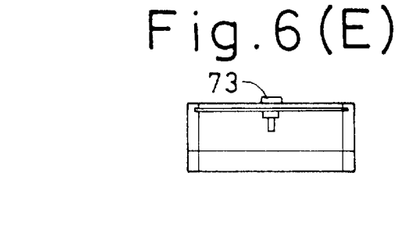

A downward pointing wedge pin 74 is anchored slightly right of the bottom center of the sliding lid 72, and when the lid 72 is moved to the left the wedge pin 74 wedges between the two pipes 76*a*, 76*b*, opening the two pipes 76*a*, 76*b* apart in a Y-shaped manner (FIG. 6(D)). In the Y-shaped space between the pipes 76*a*, 76*b*, an operator (not shown) mounts a new test tube 42 in the rotating cylinder 52, or removes a test tube 42 which has already been measured. When the lid 72 is closed, the wedge pin 74 is released from between the pipes 76*a*, 76*b* so that the two pipes 76*a*, 76*b* are restored by their own elasticity to a parallel state (FIG. 6(C)). Numeral 75 is a stopper positioned in contact with the side wall 71*a* in order to ensure an appropriate degree of wedging of the wedge pin 74 when the lid 72 has been opened (FIG. 6(D)).

Figure 7:
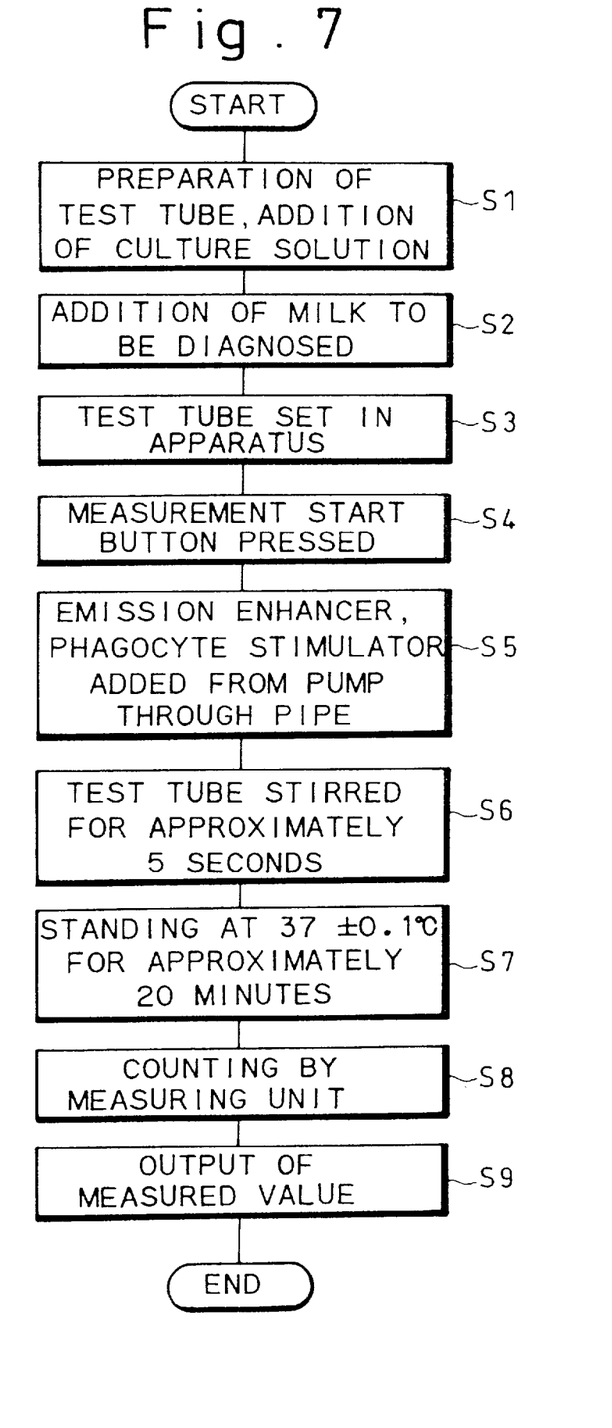
FIG. 7 is a flow chart showing the operation of the mastitis diagnosing apparatus according to this embodiment.

The operation of the mastitis diagnosing apparatus D constructed in this manner will now be explained primarily with reference to the flow chart shown in FIG. 7.

First, a silicon-coated test tube 42 is prepared, 450 $\mu$l of a solution of E-MEM (Eagle's Minimum Essential Medium) is poured in as the culture solution (step S1), and then 50 $\mu$l of milk to be diagnosed is added (step S2) prior to setting the test tube 42 in the mastitis diagnosing apparatus D (step S3).

Specifically, the cover 1*b* of the mastitis diagnosing apparatus D is opened (FIG. 1(B)), and then the sliding lid 72 is slid to the left causing the wedge pin 74 to wedge between the two pipes 76*a*, 76*b*, thus opening the two pipes apart in a Y-shaped manner (FIGS. 6(A), (D)). After inserting the milk-containing test tube 42 through the Y-shape opened gap into the circular hole of the test tube anchoring rubber piece 52*a* and setting the test tube 42 by pressing it inward to the desired depth (FIG. 2(A)) the sliding lid 72 and cover 1*b* are closed. Opening and closing of the cover 1*b* are detected by the microswitch 6 (FIG. 1), while opening and closing of the sliding lid 72 are detected by the microswitch 77 (FIG. 2). Upon detection by these switches 6, 77, the controller 10 determines that the apparatus is in an operable state.

Next, the measurement initiating button (start button) 21 is pressed (step S4), 10 $\mu$l of the emission enhancer luminol is transported through the pipe 76*a* while 10 $\mu$l of the phagocyte stimulator zymosan is transported through the pipe 76*b*, from the reagent injection pump 2 (FIGS. 1(A), (B)), and the two solutions are simultaneously injected into the test tube 42 (step S5).

Figure 8A:
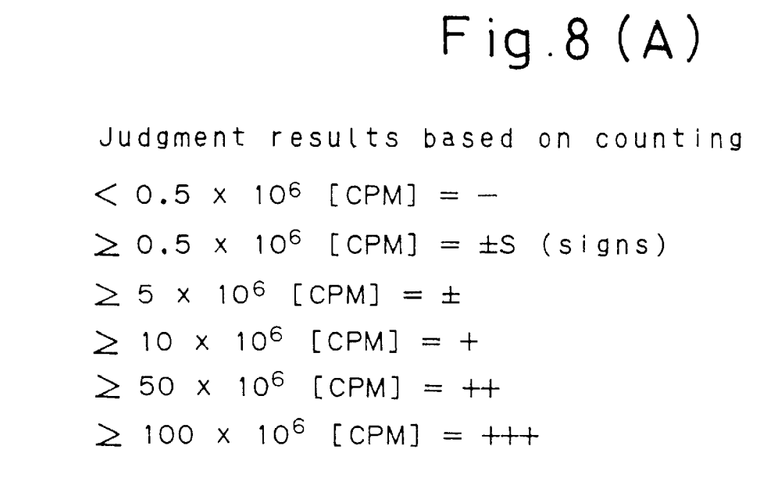
FIGS. 8(A) and 8(B) are illustrative representations of the results of operating a mastitis diagnosing apparatus according to this embodiment, wherein 8(A) shows the correspondence between count number and diagnosis results, and 8(B) shows a printed output for the state of progression of mastitis corresponding to the diagnosis results.

Operation of the stirrer 50 rotates the test tube 42 in forward and reverse causing stirring for about 5 seconds, thus thoroughly mixing the E-MEM solution, milk, emission enhancer and phagocyte stimulator (step S6). A current is then fed to the film heater 53 to keep the test tube 42 at a constant temperature (37±0.1° C.) under the control of the temperature adjuster 12, and this is maintained for about 20 minutes for incubation of the bacteria and phagocytic leukocytes (step S7) The shutter 60 (FIGS. 1, 2, 5) is then operated by instructions from the shutter open/close controller 15 to open the shutter plate 64 for about one minute, during which time the photons chemically emitted from inside the test tube 42 are detected by the photodetector 41*a* of the measuring unit 41, and counted by the counter 11 (step S8). Based on the counted value during one minute (unites: CPM), the extractor/converter 13 extracts the state of progression corresponding to the counted value from the mastitis progression data memory 80, converts it to a judgment value such as "±S, ++" (see FIG. 8(A)), and displays it on the display 31 (FIG. 1(A)), or if the print start button 33 has been pressed, it prints out the judgment value from a printer 32 (FIG. 8(A)) (step S9).

Figure 8B:
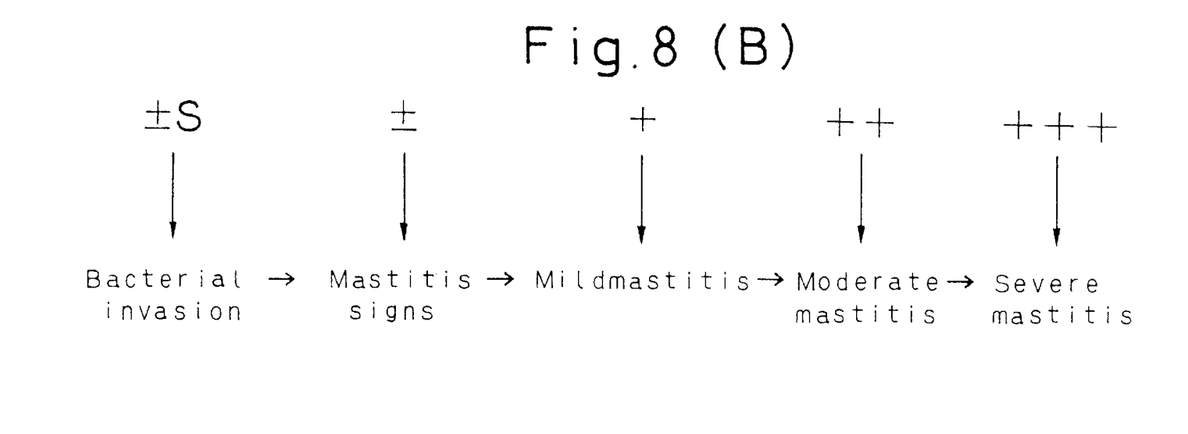

The relationship between the judgment value and the course of mastitis is the relationship shown in FIG. 8(B), and thus a value of "±S", for example, gives a printed output of "mastitis signs", so that the diagnosis of the progression of mastitis can be made at a glance.

Incidentally, in the present embodiment a commercial power source (100V AC) was used as the power source, but a conveniently portable battery operated type may also be used, considering situations in which the diagnosis of mastitis is made at a cowhouses where dairy cows are raised.

Also, while luminol was used as the emission enhancer in this case for the present embodiment, there may also be used lucigenin, Vargula hilgendorfii luciferin derivatives, and the like.

In addition, although zymosan was used as the phagocyte stimulator in this case for the present embodiment, there may also be used ConA (Concanavalin A), PHA (Phytohemagglutinin), PWM (Pokeweed Mitogen) and the like.

What is claimed is:

1. A mastitis diagnosing apparatus comprising:
   a memory which stores a corresponding relationship between the number of photons emitted in proportion to the amount of active oxygen released when phagocytic leukocytes phagocytose bacteria in milk and the degree of progression of mastitis due to said bacteria;
   photon counting means which counts within a prescribed period of time the number of photons emitted in proportion to the amount of active oxygen released when phagocytic leukocytes in milk phagocytose bacteria, by addition of a culture solution, emission enhancer and phagocyte stimulator to the milk itself;

diagnosing means which refers to said memory and, based on the number of photons counted by the photon counting means, diagnoses the degree of progression of mastitis corresponding to said number of photons; and output means which outputs the degree of progression of mastitis diagnosed by the diagnosing means.

2. A mastitis diagnosing apparatus according to claim 1, wherein said photon counting means includes at least a photodetector having a photoelectron multiplier tube.

3. A mastitis diagnosing apparatus according to claim 1, characterized in that said output means includes at least either a liquid crystal display device or a printer.

4. A mastitis diagnosing apparatus comprising:

a memory which stores a corresponding relationship between the number of photons emitted in proportion to the amount of active oxygen released when phagocytic leukocytes phagocytose bacteria in milk and the degree of progression of mastitis due to said bacteria;

reagent injection means which injects an emission enhancer and phagocyte stimulator into a set test tube in which the milk itself and a culture solution are mixed;

stirring means which stirs with a prescribed period of stirring the test tube into which the emission enhancer and phagocyte stimulator have been injected from the reagent injection means;

incubation means which keeps the test tube stirred by the stirring means at a constant temperature;

photon counting means which counts within a prescribed period of time the number of photons emitted when bacteria are phagocytosed by phagocytic leukocytes contained in the milk in the test tube incubated by the incubation means;

diagnosing means which refers to said memory and, based on the number of photons counted by the photon counting means, diagnoses the degree of progression of mastitis corresponding to said number of photons; and output means which outputs the degree of progression of mastitis diagnosed by the diagnosing means.

5. A mastitis diagnosing apparatus according to claim 4, wherein said photon counting means includes at least a photodetector having a photoelectron multiplier tube.

6. A mastitis diagnosing apparatus according to claim 4, wherein said reagent injection means includes at least a pump having a tank section said tank section including the emission enhancer and the phagocyte stimulator.

7. A mastitis diagnosing apparatus according to claim 4, characterized in that said output means includes at least either a liquid crystal display device or a printer.

8. A mastitis diagnosing apparatus according to claim 4, wherein said stirring means includes at least a cylindrical rotating cylinder for holding the test tube, a forward/reverse rotatable stepping motor and a belt looped between the cylindrical rotating cylinder and the forward/reverse rotatable stepping motor.

9. A mastitis diagnosing apparatus according to claim 4, wherein said incubation means includes at least a film heater equipped with a temperature detecting sensor for maintaining a constant temperature.

* * * * *